US008485025B2

(12) United States Patent
Woody et al.

(10) Patent No.: US 8,485,025 B2
(45) Date of Patent: Jul. 16, 2013

(54) STANDING WAVE FIBERS FOR THE DETECTION OF NUCLEIC ACIDS

(75) Inventors: Shane Woody, Charlotte, NC (US); Jennifer Weller, Charlotte, NC (US)

(73) Assignee: InSituTec, LLC, Concord, NC (US)

( * ) Notice: Subject to any disclaimer, the term of this patent is extended or adjusted under 35 U.S.C. 154(b) by 362 days.

(21) Appl. No.: 12/851,220

(22) Filed: Aug. 5, 2010

(65) Prior Publication Data

US 2010/0297746 A1    Nov. 25, 2010

Related U.S. Application Data

(63) Continuation-in-part of application No. 11/956,915, filed on Dec. 14, 2007, and a continuation-in-part of application No. 12/395,213, filed on Feb. 27, 2009.

(60) Provisional application No. 61/231,357, filed on Aug. 5, 2009.

(51) Int. Cl.
*G01B 5/28* (2006.01)
*G01N 29/02* (2006.01)

(52) U.S. Cl.
USPC .......... 73/105; 73/24.02; 73/24.06; 73/61.79; 73/64.53

(58) Field of Classification Search
USPC .............. 73/105, 24.01, 24.06, 61.41, 61.79, 73/64.53
See application file for complete search history.

(56) References Cited

U.S. PATENT DOCUMENTS

| 5,247,751 | A | 9/1993 | Ohya et al. | |
|---|---|---|---|---|
| 5,461,907 | A | 10/1995 | Tench et al. | |
| 6,246,054 | B1 | 6/2001 | Toda et al. | |
| 6,452,171 | B1 * | 9/2002 | Moloni | 850/57 |
| 6,862,921 | B2 | 3/2005 | Chand et al. | |
| 6,918,286 | B2 | 7/2005 | Kitazawa et al. | |
| 6,955,078 | B2 | 10/2005 | Mancevski et al. | |
| 7,137,291 | B2 | 11/2006 | Mancevski | |
| 7,278,297 | B2 | 10/2007 | Bauza et al. | |
| 8,215,170 | B2 * | 7/2012 | Tao et al. | 73/579 |
| 2002/0005062 | A1 | 1/2002 | Matsuki et al. | |
| 2003/0011389 | A1 | 1/2003 | Nakayama et al. | |
| 2005/0199047 | A1 * | 9/2005 | Adams et al. | 73/105 |
| 2005/0208304 | A1 * | 9/2005 | Collier et al. | 428/403 |

OTHER PUBLICATIONS

Boussaad, S. et al., "Polymer Wire Channel Sensor Using a Microfabricated Tuning Fork", Nano Letters, vol. 3, No. 8, 2003, pp. 1173-1176.*

(Continued)

*Primary Examiner* — Daniel Larkin
(74) *Attorney, Agent, or Firm* — Clements Bernard PLLC; Christopher L. Bernard; Lawrence A. Baratta, Jr.

(57) ABSTRACT

The present invention provides a standing wave fiber assembly for the collection and detection of a biological target in a complex biological fluid, including: an oscillator; and an elongated fiber coupled to the oscillator, wherein the elongated fiber is selectively exposed to a fluid potentially containing the biological target, and wherein the resonated elongated fiber attracts the biological target, and wherein a change in a response of the resonated elongated fiber indicates the presence of the biological target. The assembly also includes a top cover plate including one or more electrical connections and a port through which the fluid is introduced. The assembly further includes a bottom cover plate including a well in which the fluid is contained. Optionally, the elongated fiber includes one or more probes homogenously functionalized along its length that bind targeted biological materials.

28 Claims, 3 Drawing Sheets

OTHER PUBLICATIONS

Kageshima, M. et al., "Noncontact Atomic Force Microscopy in Liquid Environment With Quartz Tuning Fork and Carbon Nanotube Probe", Applied Surface Science, vol. 188, 2002, pp. 440-444.*

Edwards, H. et al., "Fast, High-Resolution Atomic Force Microscopy Using a Quartz Tuning Fork as Actuator and Sensor", J. Appl. Phys., vol. 82, No. 3, Aug. 1, 1997, pp. 980-984.*

Karrai, K. et al., "Piezoelectric Tip-Sample Distance Control for Near Field Optical Microscopes", Appl. Phys. Lett., vol. 66, No. 14, Apr. 3, 1995, 1842-1844.*

Cui, Y. et al., "Nanowire Nanosensors for Highly Sensitive and Selective Detection of Biological and Chemical Species", Science, vol. 293, Aug. 17, 2001, pp. 1289-1292.*

Ramanathan, T. et al., "Amino-Functionalized Carbon Nanotubes for Binding to Polymers and Biological Systems", Chem. Mater., 2005, vol. 17, pp. 1290-1295.*

Chen, R. et al., "Noncovalent Sidewall Functionalization of Single-Walled Carbon Nanotubes for Protein Immobilization", J. Am. Chem. Soc., vol. 123, 2001, pp. 3838-3839.*

Seiji Akita and Yoshikazu Nakayama, "Manipulation of Nanomaterial by Carbon Nanotube Nonotweezers in Scanning Probe Microscope", Jpn. J. Appl. Phys. vol. 42 (2002) Pt. 1, No. 6B.

A. Schirmeisen, G. Cross, A. Stalder, P. Grutter, U. Durig, "Metallic Adhesion Forces and Tunneling Between Atomically Defined Tip and Sample", Applied Surface Science 157 (2002) 274-279.

Yantao Shen, Ning Xi, Kikng W.C. Lai and Wen F. Li, "Research Article—A novel PVDF microforce/force rate sensor for practical applications in micromanipulation", Sensor Review, vol. 24, No. 3, 2004, pp. 274-283.

Basarab G. Hosu and Karoly Jakab, "Magnetic tweezers for intracellular applications", Review of Scientific Instruments, vol. 74, No. 9, Sep. 2003 American Institute of Physics.

Marcin B. Bauza, Robert J. Hocken, and Stuart T. Smith, "Development of a virtual probe tip with an application to high aspect ratio microscale features", Review of Scientific Instruments 76, 095112, 2005 American Institute of Physics. (2005).

S. Fatikow, J. Seyfried, St. Fahlbusch, A. Buerkle, and F. Schmoeckel, A Flexible Microbot-Based Microassembly Station, Journal of Intelligent and Robotic Systems 27; 135-169, 2000 Kluwer Academic Publishers.

Hongyu Yu, Jae Wan Kwon, and Eun Sok Kim, "Microfluidic Mixer and Transporter Based on PZT Self-Focusing Acoustic Transducers", Journal of Microelectromechanical Systems, vol. 15, No. 4, Aug. 2006.

J. Zhang, S. O'Shea, "Tuning forks as micromechanical mass sensitive sensors for bio- or liquid detection", Available online at www.sciencedirect.com, Received Oct. 25, 2002.

Nardo Ramirez Frometa, "Cantilever Biosensors", Nov. 2006, vol. 23, No. 4.

Nam-Trung Nguyen, and Zhigang Wu, "Micromixers-a review", Journal of Micromechanics and Microengineering, Institute of Physics Publishing(c) 2005 IOP Publishing Ltd.

Volker Hessel, Holger Lowe, Friedhelm Schonfeld, "Topical Review—Micromixers—a reivew on passive and active mixing principles", Chemical Engineering Science, (c) 2005 Elsevier Ltd.

Shane C. Woody, Stuart T. Smith, "Resonance-based vector touch sensors", Available online at wwwl.sciencedirect.com, Precision Engineering, May 2, 2002, (c) 2003 Elsevier Inc.

Martin Guthold, Michael R. Falvo, W. Garrett Matthews, Scott Paulson, Sean Washburn, Dorothy A. Erie, Richard Superfine, Frederick P. Brooks, Jr., and Russell M. Taylor II, "Controlled Manipulatiom of Molecuar Samples with the nanoManipulator", IEEE/ASME Transactions on Mechatronics, vol. 5, No. 2, Jun. 2000.

R. Resch, D. Lewis, S. Meltzer, N. Montoya, B.E. Koel, A. Madhukar, A.A.G. Requicha, P. Will, "Manipulation of gold nanoparticles in liquid environmentals using scanning force microscopy", Ultramicroscopy 82 (2000) 35-139.

Nicolas Garnier, Roman O. Grigoriev, and Michael F. Schatz, "Optical Manipulation of Microscale Fluid Flow", Physical Review Letters, vol. 9, No. 5, Aug. 1, 2003. The American Physical Society.

* cited by examiner

STANDING WAVE FIBERS FOR THE DETECTION OF NUCLEIC ACIDS

CROSS-REFERENCE TO RELATED APPLICATIONS

The present patent application/patent claims the benefit of priority of U.S. Provisional Patent Application No. 61/231,357, filed on Aug. 5, 2009, and entitled "STANDING WAVE FIBERS FOR THE DETECTION OF NUCLEIC ACIDS," the contents of which are incorporated in full by reference herein. The present patent application/patent is also a continuation-in-part of co-pending U.S. patent application Ser. No. 11/956,915, filed on Dec. 14, 2007, and entitled "MULTI-DIMENSIONAL STANDING WAVE PROBE FOR MICROSCALE AND NANOSCALE MEASUREMENT, MANIPULATION, AND SURFACE MODIFICATION," and U.S. patent application Ser. No. 12/395,213, filed on Feb. 27, 2009, and entitled "STANDING WAVE FLUIDIC AND BIOLOGICAL TOOLS," the contents of both of which are incorporated in full by reference herein. The present patent application/patent further incorporates by reference both U.S. Pat. No. 7,278,297, issued on Oct. 9, 2007, and entitled "OSCILLATING PROBE WITH A VIRTUAL PROBE TIP," and U.S. Pat. No. 7,735,358, issued on June 15, 2010, and entitled "SELF-SENSING TWEEZER DEVICES AND ASSOCIATED METHODS FOR MICRO AND NANO-SCALE MANIPULATION AND ASSEMBLY."

FIELD OF THE INVENTION

The present invention relates generally to standing wave fibers for the detection of nucleic acids. More specifically, the present invention provides a disposable tool that can rapidly concentrate targeted agents in complex biological fluids and, with high specificity, detect these targeted agents—making the rapid and cost-effective detection/diagnosis of minute quantities of pathogens in such complex biological fluids possible.

BACKGROUND OF THE INVENTION

There is currently no known single platform that can rapidly concentrate targeted agents in complex biological fluids (e.g. saliva, sweat, urine, blood, drinking water) and, with high specificity, detect these targeted agents. The diagnostic technology of the present invention, however, enables a single, cost-effective solution for the rapid nucleic acid recognition of low concentrations of pathogens (i.e. less than 1 pg/ml) in about 30 seconds in a compact modular device that is disposable and eco-friendly. This enables the rapid detection of wide variety of pathogens with high specificity for remote villages of third world countries, for example, where access to health care facilities is minimal or non-existent. This also enables the rapid monitoring of pathogens in drinking water, for example.

Commonly assigned U.S. Pat. Nos. 7,278,297, 7,735,358, U.S. patent application Ser. No. 11/956,915, and U.S. patent application Ser. No. 12/395,213 generally disclose a novel standing wave fiber technology that can be used for mixing, vortexing, sheparding, and detection applications in fluids. As used herein, these standing wave fibers are referred to as elastic wave detector (EwD) fibers. These EwD fibers enable the detection of low concentrations of bacteria (less than 1 pg/ml) in about 30 seconds in a compact, inexpensive, and disposable cartridge. A standing wave generated in the EwD fiber (about 9 microns in diameter and about 2 mm in length, for example) while immersed in a high-enrichment sample transfers its kinetic energy effectively into the liquid and produces vortex flow patterns in the microenvironment around the EwD fiber which cause the rapid migration of solutes (such as nucleic acids or proteins after lysing protocols) towards the EwD fiber, in seconds and without degradation. Hybridization rates of low concentrations of nucleic acids (less than about 0.1 ng/ml) are accelerated using EwD fibers to create homogenous mixing and enhanced bio-kinetics by inducing ultrasonic quadrupole vortices the sample. Importantly, oligonucleotide probes functionalized to the modulating EwD fibers rapidly hybridize the target as nucleic acids are captured close and bind specifically to the EwD fibers. A variety of detection methods are available. Thus, EwD fibers enable a single platform to concentrate, capture, and detect one or more bacterial genes simultaneously, at low concentrations, and permit purification and diagnostic methods that vastly exceed the speed, sensitivity, and specificity of currently-available platforms.

BRIEF SUMMARY OF THE INVENTION

In one exemplary embodiment, the present invention provides a standing wave fiber assembly for the collection and detection of a biological target in a complex biological fluid, including: an oscillator; and an elongated fiber coupled to the oscillator, wherein the elongated fiber is selectively exposed to a fluid potentially containing the biological target, and wherein the resonated elongated fiber attracts the biological target, and wherein a change in a response of the resonated elongated fiber indicates the presence of the biological target. Optionally, the oscillator is a monolithic tuning fork. Optionally, the oscillator is manufactured on a chip. The assembly also includes a top cover plate including one or more electrical connections and a port through which the fluid is introduced. The assembly further includes a bottom cover plate including a well in which the fluid is contained. Optionally, the elongated fiber includes one or more probes homogenously functionalized along its length that bind targeted biological materials. Optionally, the elongated fiber includes one or more oligonucleotide probes homogenously functionalized along its length that bind targeted nucleic acids. Optionally, the assembly still further includes additional elongated fibers coupled to the oscillator, wherein the additional elongated fibers are selectively exposed to the fluid potentially containing additional biological targets, and wherein the resonated additional elongated fibers attract the additional biological targets, and wherein a change in a response of the resonated additional elongated fibers indicates the presence of the additional biological targets.

In another exemplary embodiment, the present invention provides a standing wave fiber method for the collection and detection of a biological target in a complex biological fluid, including: providing an oscillator; and providing an elongated fiber coupled to the oscillator, wherein the elongated fiber is selectively exposed to a fluid potentially containing the biological target, and wherein the resonated elongated fiber attracts the biological target, and wherein a change in a response of the resonated elongated fiber indicates the presence of the biological target. Optionally, the oscillator is a monolithic tuning fork. Optionally, the oscillator is manufactured on a chip. The method also includes providing a top cover plate including one or more electrical connections and a port through which the fluid is introduced. The method further includes providing a bottom cover plate including a well in which the fluid is contained. Optionally, the elongated fiber includes one or more probes homogenously functionalized along its length that bind targeted biological materials. Optionally, the elongated fiber includes one or more oligonucleotide probes homogenously functionalized along its length that bind targeted nucleic acids. Optionally, the method still further includes providing additional elongated fibers coupled to the oscillator, wherein the additional elongated fibers are selectively exposed to the fluid potentially containing additional biological targets, and wherein the resonated additional elongated fibers attract the additional biological targets, and wherein a change in a response of the resonated additional elongated fibers indicates the presence of the additional biological targets.

In a further exemplary embodiment, the present invention provides a standing wave fiber assembly for the collection and detection of a biological target in a complex biological fluid, including: an oscillator; an elongated fiber coupled to the oscillator, wherein the elongated fiber is selectively exposed to a fluid potentially containing the biological target, and wherein the resonated elongated fiber attracts the biological target, and wherein a change in a response of the resonated elongated fiber indicates the presence of the biological target; a top cover plate including one or more electrical connections and a port through which the fluid is introduced; and a bottom cover plate including a well in which the fluid is contained. Optionally, the oscillator includes a monolithic tuning fork. Optionally, the oscillator is manufactured on a chip. Optionally, the elongated fiber includes one or more probes homogenously functionalized along its length that bind targeted biological materials. Optionally, the elongated fiber includes one or more oligonucleotide probes homogenously functionalized along its length that bind targeted nucleic acids. Optionally, the assembly also includes additional elongated fibers coupled to the oscillator, wherein the additional elongated fibers are selectively exposed to the fluid potentially containing additional biological targets, and wherein the resonated additional elongated fibers attract the additional biological targets, and wherein a change in a response of the resonated additional elongated fibers indicates the presence of the additional biological targets.

BRIEF DESCRIPTION OF THE DRAWINGS

The present invention is illustrated and described herein with reference to the various drawings, in which like reference numbers are used to denote like system components/method steps, as appropriate, and in which.

DETAILED DESCRIPTION OF THE INVENTION

Again, the EwD fibers of the present invention enable the detection of low concentrations of bacteria (less than 1 pg/ml) in about 30 seconds in a compact, inexpensive, and disposable cartridge. A standing wave generated in the EwD fiber (about 9 microns in diameter and about 2 mm in length, for example) while immersed in a high-enrichment sample transfers its kinetic energy effectively into the liquid and produces vortex flow patterns in the microenvironment around the EwD fiber which cause the rapid migration of solutes (such as nucleic acids or proteins after lysing protocols) towards the EwD fiber, in seconds and without degradation. Hybridization rates of low concentrations of nucleic acids (less than about 0.1 ng/ml) are accelerated using EwD fibers to create homogenous mixing and enhanced bio-kinetics by inducing ultrasonic quadrupole vortices the sample. Importantly, oligonucleotide probes functionalized to the modulating EwD fibers rapidly hybridize the target as nucleic acids are captured close and bind specifically to the EwD fibers. A variety of detection methods are available. Thus, EwD fibers enable a single platform to concentrate, capture, and detect one or more bacterial genes simultaneously, at low concentrations, and permit purification and diagnostic methods that vastly exceed the speed, sensitivity, and specificity of currently-available platforms.

Figure 1:
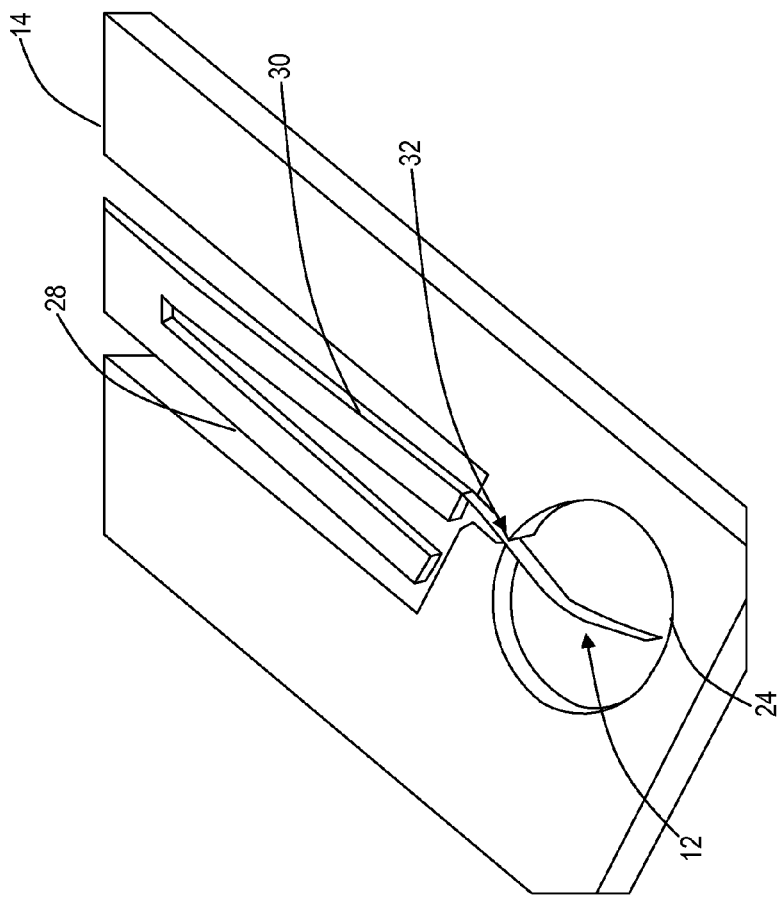
FIG. 1 is a series of schematic diagrams illustrating one exemplary embodiment of the EwD fiber assembly of the present invention.
Figure 1:
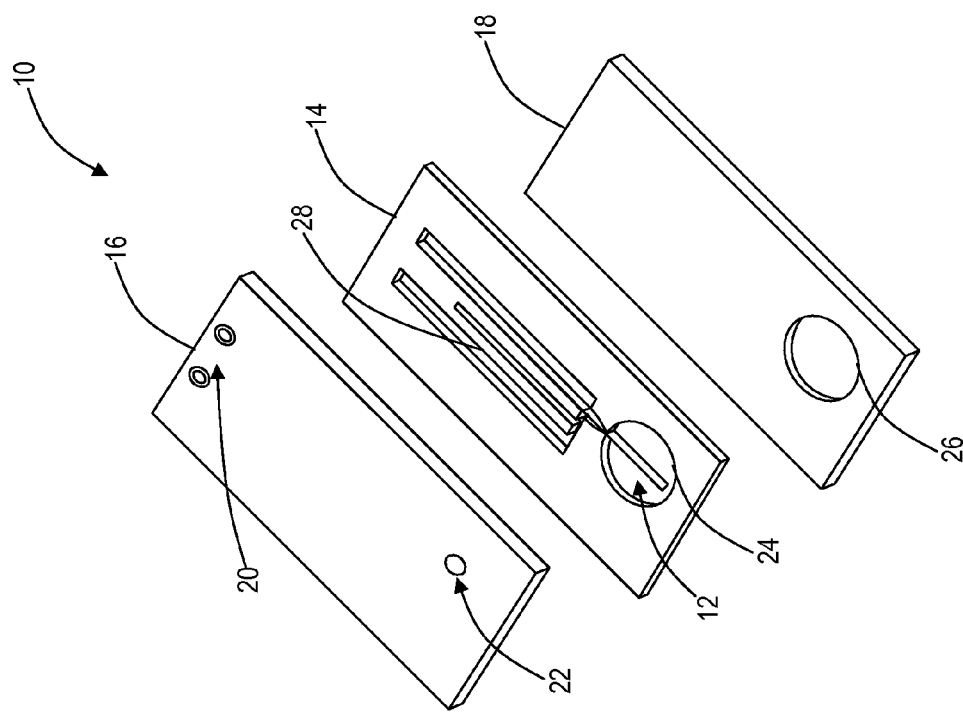
Figure 2:
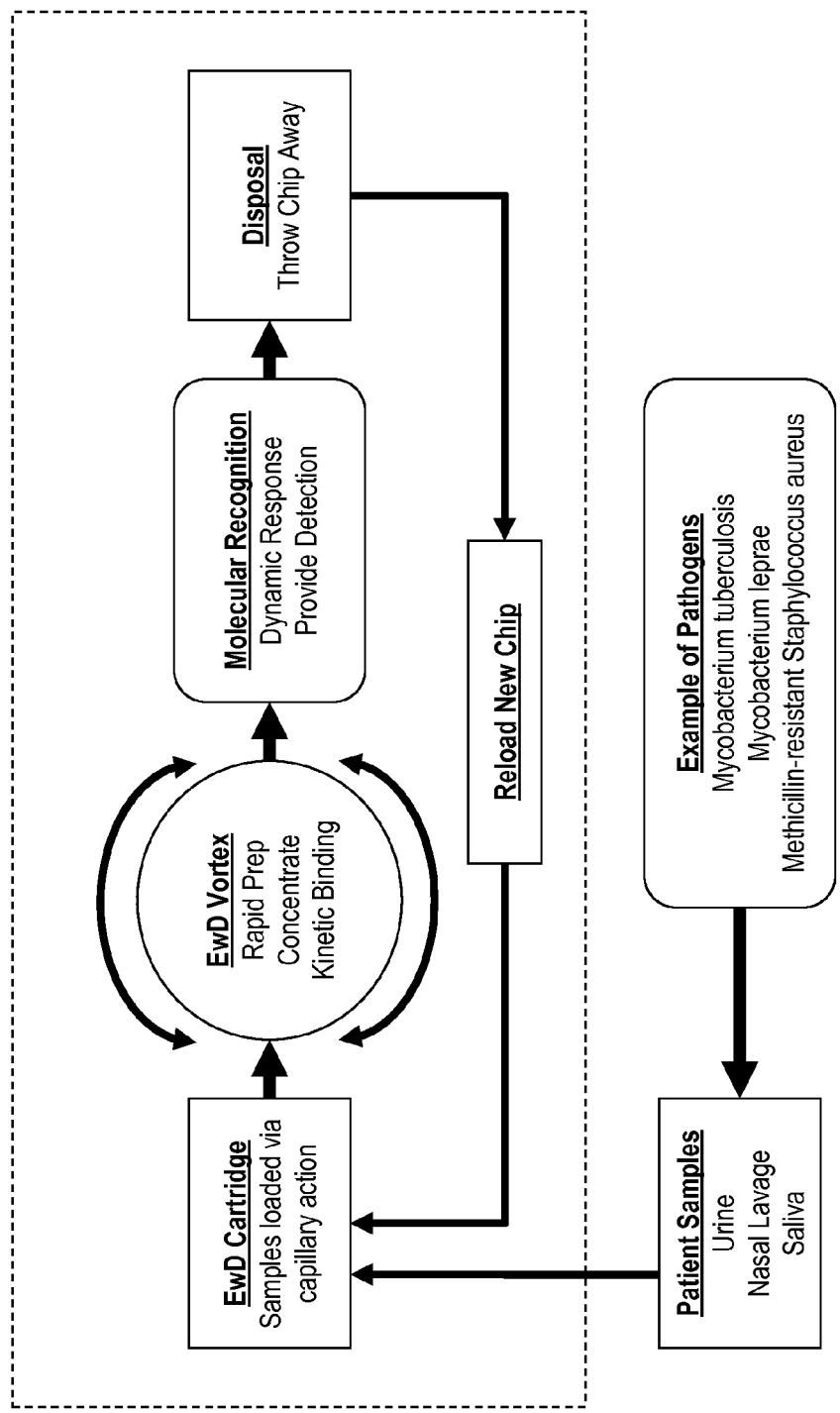
FIG. 2 is a flowchart illustrating loading a sample, vortexing to attract a target, performing molecular recognition, disposing of a chip, and reloading a new chip in accordance with the systems and methods of the present invention.

Referring to FIG. 1, the EwD fiber assembly 10 of the present invention represents a new class of actuator/sensor and includes a highly elastic microscale fiber 12 that is modulated at about 32 kHz and produces pronounced mechanical waves in a fluid sample. Tip velocities of the EwD fiber 12 are programmable and exceed 10 m/s in gas environments and 3 m/s in liquid environments. A striking quadrupole flow pattern is generated in fluidic environments, wherein several interesting hydrodynamic phenomena have been observed, including wide spanning vortices reaching 300× the distance of the EwD fiber 12 and fluid velocities exceeding 1 m/s. Furthermore, the EwD fibers 12 apparently have no degradative effect on cell viability (based on standard spread plate analysis) with bacteria and with strand length for dsDNA during vortexing. The EwD fibers 12 are able to trap and collect bacteria in less than about 10 seconds in concentrations of about $10^4$/ml. This unique vortexing and microscale structure opens a unique opportunity in the rapid collection of biological samples.

Thus, the EwD fiber assembly 10 transfers a wide ranging vortex into fluidic samples, rapidly pulls cells or nucleic acids into proximity, and due to the high local concentration, enhances the rate of binding to functional groups attached to the EwD fiber 12. This diagnostic methodology enables the fabrication of miniaturized, highly specific, and low cost cartridges. In one exemplary embodiment, the EwD fiber assembly 10 takes the form of a chip. The EwD actuator/sensor 14 is disposed between a top cover plate 16 and a bottom cover plate 18. The top cover plate 16 provides electrical connections 20 that transfer input and output signals to and from the EwD actuator/sensor 14, and includes a port 22 through which a fluidic sample is pipetted or otherwise introduced. By way of example, the top cover plate 16 and bottom cover plate 18 can be made of quartz or any suitable natural or synthetic material and have dimensions of between a few millimeters and hundreds of millimeters, although other suitable materials and dimensions may be utilized. The port 22 is in fluid communication with a hole 24 manufactured into the EwD actuator/sensor 14 and a well 26 manufactured into the bottom cover plate 18, collectively forming a microscale chamber in which a fluidic sample is contained for analysis. The EwD actuator/sensor 14 is manufactured from a fused quartz wafer or the like (using lithography techniques), which is naturally poled and transparent. This chip consists of an electromechanical monolithic tuning fork 28 in a "dry" environment, high aspect ratio beam 12, and the above-mentioned well 26. The tuning fork 28 represents an oscillator, also referred to more narrowly as a resonator, which is a subset thereof. The elongated beam 12 is coupled to the end of the tuning fork's tine 30 and passes through a narrow channel 32 and into the sample chamber. The tuning fork 28 is actuated at its resonance frequency and provides a base excitation to the cantilever 12. The structure is tuned such that the rod's nodal position, located along the length of the rod 12, is positioned at the intersection of the microchannel opening and from there protrudes into the sample chamber. Oligonucleotide probes are homogenously functionalized along the glass fiber 12 and will bind targeted nucleic acids. A single platform solution fashioned from naturally poled quartz wafers enables a chip that can be mass produced and thrown away. The transparent nature of quartz further enables the ability to use an external fluorometer to monitor the fluorescence of the fiber 12 in-situ during the hybridization step. It will be readily apparent to those of ordinary skill in the art that the physical/structural configuration illustrated and described herein has many functional equivalents. These functional equivalents are all contemplated by the present invention. Importantly, as used herein (including in the claims), the term elongated fiber is intended to refer to any physical structure in which a standing wave can be generated, of any shape, of any dimensions, of constant or varying dimensions, whether singly or multiply constrained, etc.

The microfluidic chamber and electromechanical parameters of the EwD fiber 12 can be varied to optimize the kinetic energy and vortexing achieved, including the EwD fiber's drive frequency, oscillation amplitude, and the details of the flow field on nucleic acid capture profiles. The hybridization rates of low concentrations of nucleic acid (<0.1 ng/ml) are accelerated using EwD fibers 12 to create homogenous mixing and greatly enhanced reaction rates by inducing ultrasonic quadrupole vortices into the sample. Small volume samples of nucleic acid and a target oligonucleotide probe can be mixed, hybridized, and detected in <10s. The response time of microarrays (expression, genotyping, and sequencing) are dramatically impacted with the employment of the EwD fibers 12, thereby leading to greater sensitivity, reproducibility, lower costs, and more efficient turn-around times for human molecular diagnostics assays. The unique vortexing capability of the EwD fibers 12 has been observed to rapidly trap nucleic acid along the fiber structure. Thus, functionalizing oligonucleotide probes to the EwD fiber 12 leads to rapid kinetic binding through hybridization of the target to the probe. Moreover, the EwD fibers 12 can be multi-functionalized with different DNA probes, and can use reporters that intensify in fluorescence upon duplex formation to obtain real-time read-outs of the presence of sequences of interest. Bioassays are often comprised of complex mixtures with multiple agents that need to be detected. In this case, the same EwD fiber assembly 10 can have multiple fibers 12 functionalized with different probes.

As alluded to above, rapid sample preparation and detection for targets is currently a challenge and can take up to 72 hours, using culture and real time PCR methods (when cells are very dilute) and 30-60 minutes using direct methods, such as ELISA (when cells do not need to be amplified). It has been shown that vortices generated by the EwD fibers 12 of the present invention concentrate bacteria (e.g. $E.\ coli$ and $S.\ aureus$) from solution to a small volume near the fiber in less than about 10 seconds with no apparent damage to the cells (prelysed) or purified chromosomal DNA based upon the viability of cells in solid culture methods and gel electrophoresis methods to assay DNA integrity. The present detection method relies on a crystal oscillator 28 providing both a base excitation to the fiber 12 and a sensing method to monitor mechanical changes in the probes response. To increase the sensitivity to resolve pathogens, which bind to the fiber in a flowing liquid, oligonucleotide probes are functionalized to the modulating fibers 12, the fibers 12 are immersed in filtered nucleic acids and generate real-time hybridization of a targeted agent to the fiber probe in seconds. Detection is achieved using fluorescent dyes combined with a fluorometer focusing on the microscale fiber structure.

The overarching objective for the EwD fiber assembly 10 is the development and commercialization of handheld detectors targeted at early and rapid detection of pathogens. For example, Methicillin-resistant *Staphylococcus aureus* (MRSA) is resistant to antibiotics and difficult to treat for human infections. Early warning detectors for pathogens such as MRSA are highly sought to minimize the spread of infection diseases and ultimately save lives.

The present invention contemplates a disposable EwD chip that loads a sample (urine, saliva, puss, or drinking water) and attracts the targeted agents in seconds to a device smaller than 1/50th the size of a human hair. Once cells are lysed, and nucleic acids filtered into the cartridge, the nucleic acids accelerate towards the modulating source. A rapid hybridization protocol is proposed by functionalizing oligonucleotide probes to the elongated fiber 12. Targeted nucleic acids kinetically bind to the probes at the annealing phase to achieve high specificity. Detection is achieved using targets end-labeled with fluorescent dyes via molecular biology methods combined with optical devices sensitive to the wavelengths of those dyes. In the presence of calibration standards, these platforms are both sensitive and quantitative. A variety of secondary assays are available for testing the limits of target capture that may fall below the optical detection limits of a scanner, including sandwich assays that provide signal amplification on the fibers 12, and quantitative PCR reactions that remove the captured material and amplify it separately.

Large arrays of EwD fiber assemblies 10 are possible because the fibers 12 are easily manufactured using current microfabrication techniques. This translates into low cost, miniaturization, and the possibility of lab-on-a-chip designs. For handheld, point-of-care units, the EwD concept can be merged with a handheld type fluorometer. The fluorescence detector should be re-engineered for optimal fluorescence readout from the fiber 12. Thus, the EwD concept can be produced as a reasonably priced, handheld, modular unit that enables third world countries to have access to improved, rapid bioassays. This technology provides the ability to test bacterial levels in drinking water supplies, collect samples for pathogens or toxin detection, and perform rapid, on-site screening diagnostics.

Figure 3:
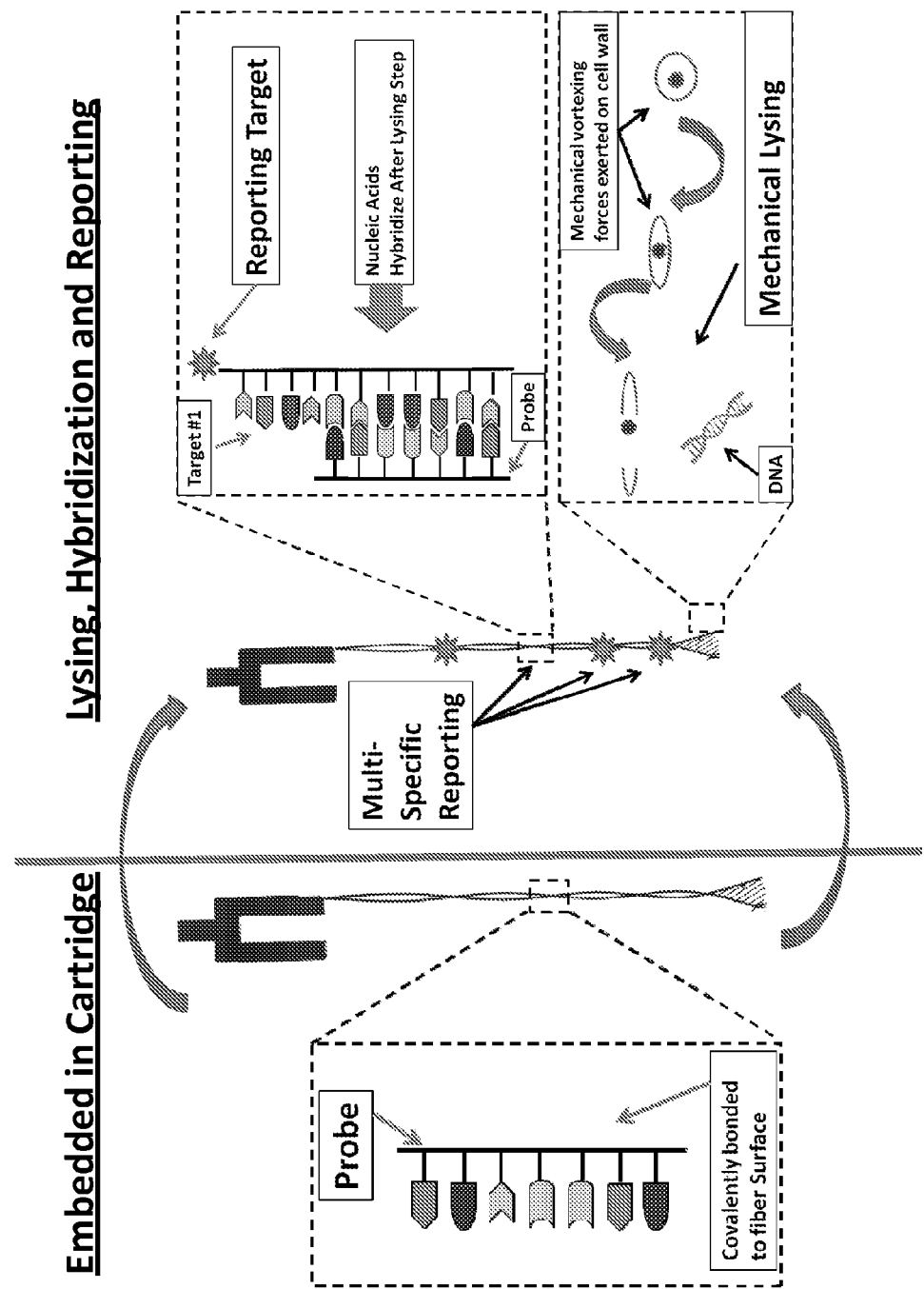
FIG. 3 is a schematic diagram illustrating another exemplary embodiment of the EwD fiber assembly of the present invention, performing lysing, oligoprobe binding, and target-specific reporting functions.

By way of summary, in a more complex configuration, the EwD fiber assemblies 10 of the present invention can include fibers 12 that are themselves functionalized with oligoprobes, or, alternatively, printed or assembled microarrays of such oligoprobes can be disposed adjacent to the fibers 12, for example. In either case, the fibers 12, when actuated, promote mixing and the like such that the hybridization kinetics of the overall system are enhanced, with enhanced binding of DNA/RNA to the oligoprobes. Thus, detection times can be decreased commensurately. In addition, the fibers 12 can be used to first lyse (or break) the cells containing the DNA/RNA prior to promoting rapid binding. (See FIG. 3). Such lysing can be enhanced via the incorporation of various chemical agents to the agitated system, such that bacteria and other pathogens with thick walls can be effectively lysed more rapidly. In all of the oligoprobe cases, multiple specific probes can be utilized relative to positions along the fibers 12, allowing for targeted reporting for different nucleic acids or targets of interest.

EXPERIMENTAL RESULTS

The fundamental operating principle of the present invention is the effective, high-Q excitation of an elastic microscale fiber, Ø9 μm, by a tuning fork oscillator which produces pronounced mechanical standing waves in the fiber that continue to propagate even in the presence of a liquid environment. The current device is fashioned from a quartz crystal tuning fork to which a microscale glass fiber is attached at the end of the tine. The fiber is modulated using the tuning fork at a drive frequency of 32,000 cycles per second and fiber velocities are programmable up to 1 m/s in liquid environments. The following sections provide preliminary experimental studies in fluid flow, molecular recognition of cell bacteria, hybridization, bio-interfacing probes to fibers, and degradation of cells and nucleic acids.

Experiments were conducted using Lagrangian particle tracking, to study the flow field generated by the vibrating fiber. Images were captured using a high-speed camera combined with a two-stage image intensifier. With this configuration, 512×512 pixel images were taken at a frame rate of 3,000 fps and an exposure time of 100 μs, which allows the particles to move several pixels in the image without streaking The energy propagation from the EwD fiber into the fluid entails the creation of quadrupolar fluid vortices that create a strong mixing effect. Mathematical streamline functions correlated experimental and theoretical 2D flow fields. Based upon this work, the center eye has fluid velocities exceeding 3 m/s near the surface of the fiber.

Target agents are pulled indiscriminately into the vortex and spin at phenomenal acceleration and velocities. The rate of spin is controlled by modulating the amplitude and frequency of the EwD. Preliminary studies show that crystal violet stained *Staphylococcus aureus cocci* (Gram-positive) and *E. coli* (Gram-negative bacilli) in $10^4$/ml, are rapidly captured in this vortexing flow field in under 10s. The fluid action caused by the probes apparently has no degradative effect on bacteria or cells using standard spread plate methods, but instead results in rapid trapping and collection of the bacteria. As a result, this significantly advances the ability to attract target analyte, even when present only at low concentration in solution (<100 CFU/ml), to the fiber surface. State-of-the-art in micromixing is unable to produce the same rapid mixing effect enabled by the EwD because the typical Reynolds numbers for micron-scale fluidic systems are small, usually <1000. In this regime, fluid flow is laminar and turbulent velocity motion is largely absent, which implies that only molecular diffusion is available for mixing. From dimensional analysis, typical timescales for laminar diffusion are given by $T_{lam}=D/L^2$ where D is the diffusion coefficient and L is the characteristic length scale of the system. For a typical biological system (e.g., mixing a moderately-sized protein in a 100 micron channel), $T_{lam}$ is ~500 s, far too long for many practical applications.

Molecular recognition of a cell, that is specific binding, has been successfully achieved. This study used etch-cleaned glass fibers immersed in a methanolic solution of aminopropyltriethoxy silane to coat the fiber surface with a self-assembled monolayer which then provides a surface for protein coupling. Protein G is conjugated covalently to the fiber surface by NHS amine coupling chemistry. The protein G has 2 Fc receptor sites to bind antibodies generically, which makes it an ideal candidate to attach many types of antibodies. The fiber with protein G was then activated in a solution of anti *S. aureus* primary antibody, followed by immersion in a solution of GFP-expressing *S. aureus* at a concentration of $10^4$/ml.

*E. coli* chromosomal DNA with mean length of ~1200 kbp was vortexed for 10 min. without significant degradation, based upon gel electrophoresis methods. Hybridization experiments were then conducted, using a fluorescent dual-labeled DNA probe. Vortexing DNA probe (0.5 μ/ml) with target (0.78 μ/ml) of similar volumes demonstrated 2× faster hybridization speeds compared to standard PCR. This was accomplished without optimizing parameters for the EwD mixing and is expected to be dramatically enhanced >10×.

The EwD fibers are available with either epoxy-silane or amino-silane coatings. Since these correspond to the functional groups present on glass slides used for the production of microarrays, several protocols for attaching amino-C6 oligodeoxyribonucleotide probes were tried. Control fibers, without labeled probes derivatized to them, were imaged, using a Tecan LS Reloaded laser scanner. Since the non-functionalized fibers do not fluoresce under the 532 laser, the image's contrast was inverted. A 24-hour incubation in slightly basic buffer and DMSO at 42° C. and high humidity gave excellent coverage of the fiber with Cy3-labeled probe for the amino-silane fibers; the epoxy-silane fibers had much less homogeneous coverage. The intensity of the Cy3 dye was used as a way to monitor the reaction. Extensive washing of the fibers did not result in loss of the dye, indicating that covalent attachment occurred. On the basis of this result, the amino-silane fiber group was functionalized with the same oligonucleotide probe lacking the fluorescent dye, and then hybridized for 14 hours at 65° C. in standard hybridization buffer that included a complementary DNA target labeled with the Cy3 dye. A non-functionalized control fiber was included to test for non-specific binding. After stringent washing in low-salt buffer, both types of fibers were imaged, and, while no apparent target is bound to the control, the functionalized fibers show complementary target has been bound. This is an end-point hybridization reaction, without the rate enhancement that mixing is expected to provide. The purpose was to demonstrate simple and specific functionalization of the fiber is possible and that the fiber does not interfere with solution hybridization. The surface area of the fiber approximates that of a 200 um diameter spot on a microarray. In order to increase the sensitivity a branched amino reactive group can be introduced, allowing the attachment of a higher density of probes.

Although the present invention has been illustrated and described herein with reference to preferred embodiments and specific examples thereof, it will be readily apparent to those of ordinary skill in the art that other embodiments and examples can perform similar functions and/or achieve like results. All such equivalent embodiments and examples are within the spirit and scope of the present invention, are contemplated thereby, and are intended to be covered by the following claims.

What is claimed is:

1. A standing wave fiber assembly for the collection and detection of a biological target in a biological fluid, comprising:
    an oscillator; and
    an elongated fiber coupled to the oscillator, wherein the elongated fiber is selectively exposed to a fluid potentially containing the biological target, and wherein the resonated elongated fiber attracts the biological target, and wherein a change in a response of the resonated elongated fiber indicates the presence of the biological target;
    wherein oscillation of the elongated fiber during at least one complete cycle of oscillation of the oscillator causes the elongated fiber to move in an envelope, producing a defined virtual geometry of the elongated fiber, wherein a shape of the virtual geometry is defined by both a characteristic shape of the oscillation of the elongated fiber and a geometry of the elongated fiber.

2. The standing wave fiber assembly of claim 1, wherein the oscillator comprises a monolithic tuning fork.

3. The standing wave fiber assembly of claim 1, wherein the oscillator is manufactured on a chip.

4. The standing wave fiber assembly of claim 1, further comprising a top cover plate comprising a port through which the fluid is introduced.

5. The standing wave fiber assembly of claim 1, further comprising a bottom cover plate comprising a well in which the fluid is contained.

6. The standing wave fiber assembly of claim 1, wherein the elongated fiber comprises one or more probes functionalized along its length that bind targeted biological materials.

7. The standing wave fiber assembly of claim 6, wherein the elongated fiber comprises one or more oligonucleotide probes functionalized along its length that bind targeted nucleic acids.

8. The standing wave fiber assembly of claim 1, further comprising one or more probes disposed adjacent to and in fluid communication with the elongated fiber.

9. The standing wave fiber assembly of claim 1, wherein the elongated fiber is operable for enhancing the hybridization kinetics in the fluid.

10. The standing wave fiber assembly of claim 1, wherein the elongated fiber is operable for lysing a biological entity prior to detecting the presence of the biological target.

11. The standing wave fiber assembly of claim 1, further comprising additional elongated fibers coupled to the oscillator, wherein the additional elongated fibers are selectively exposed to the fluid potentially containing additional biological targets, and wherein the resonated additional elongated fibers attract the additional biological targets, and wherein a change in a response of the resonated additional elongated fibers indicates the presence of the additional biological targets.

12. A standing wave fiber method for the collection and detection of a biological target in a complex biological fluid, comprising:
 providing an oscillator; and
 providing an elongated fiber coupled to the oscillator, wherein the elongated fiber is selectively exposed to a fluid potentially containing the biological target, and wherein the resonated elongated fiber attracts the biological target, and wherein a change in a response of the resonated elongated fiber indicates the presence of the biological target;
 wherein oscillation of the elongated fiber during at least one complete cycle of oscillation of the oscillator causes the elongated fiber to move in an envelope, producing a defined virtual geometry of the elongated fiber, wherein a shape of the virtual geometry is defined by both a characteristic shape of the oscillation of the elongated fiber and a geometry of the elongated fiber.

13. The standing wave fiber method of claim 12, wherein the oscillator comprises a monolithic tuning fork.

14. The standing wave fiber method of claim 12, wherein the oscillator is manufactured on a chip.

15. The standing wave fiber method of claim 12, further comprising providing a top cover plate comprising a port through which the fluid is introduced.

16. The standing wave fiber method of claim 12, further comprising providing a bottom cover plate comprising a well in which the fluid is contained.

17. The standing wave fiber method of claim 12, wherein the elongated fiber comprises one or more probes functionalized along its length that bind targeted biological materials.

18. The standing wave fiber method of claim 17, wherein the elongated fiber comprises one or more oligonucleotide probes functionalized along its length that bind targeted nucleic acids.

19. The standing wave fiber method of claim 12, further comprising providing one or more probes disposed adjacent to and in fluid communication with the elongated fiber.

20. The standing wave fiber method of claim 12, wherein the elongated fiber is operable for enhancing the hybridization kinetics in the fluid.

21. The standing wave fiber method of claim 12, wherein the elongated fiber is operable for lysing a biological entity prior to detecting the presence of the biological target.

22. The standing wave fiber method of claim 12, further comprising providing additional elongated fibers coupled to the oscillator, wherein the additional elongated fibers are selectively exposed to the fluid potentially containing additional biological targets, and wherein the resonated additional elongated fibers attract the additional biological targets, and wherein a change in a response of the resonated additional elongated fibers indicates the presence of the additional biological targets.

23. A standing wave fiber assembly for the collection and detection of a biological target in a complex biological fluid, comprising:
 an oscillator;
 an elongated fiber coupled to the oscillator, wherein the elongated fiber is selectively exposed to a fluid potentially containing the biological target, and wherein the resonated elongated fiber attracts the biological target, and wherein a change in a response of the resonated elongated fiber indicates the presence of the biological target;
 a top cover plate comprising a port through which the fluid is introduced; and
 a bottom cover plate comprising a well in which the fluid is contained;
 wherein oscillation of the elongated fiber during at least one complete cycle of oscillation of the oscillator causes the elongated fiber to move in an envelope, producing a defined virtual geometry of the elongated fiber, wherein a shape of the virtual geometry is defined by both a characteristic shape of the oscillation of the elongated fiber and a geometry of the elongated fiber.

24. The standing wave fiber assembly of claim 23, wherein the oscillator comprises a monolithic tuning fork.

25. The standing wave fiber assembly of claim 23, wherein the oscillator is manufactured on a chip.

26. The standing wave fiber assembly of claim 23, wherein the elongated fiber comprises one or more probes functionalized along its length that bind targeted biological materials.

27. The standing wave fiber assembly of claim 26, wherein the elongated fiber comprises one or more oligonucleotide probes functionalized along its length that bind targeted nucleic acids.

28. The standing wave fiber assembly of claim 23, further comprising additional elongated fibers coupled to the oscillator, wherein the additional elongated fibers are selectively exposed to the fluid potentially containing additional biological targets, and wherein the resonated additional elongated fibers attract the additional biological targets, and wherein a change in a response of the resonated additional elongated fibers indicates the presence of the additional biological targets.

* * * * *